(12) United States Patent
Koulik

(10) Patent No.: US 7,014,610 B2
(45) Date of Patent: Mar. 21, 2006

(54) ECHOGENIC DEVICES AND METHODS OF MAKING AND USING SUCH DEVICES

(75) Inventor: Edouard Koulik, Golden Valley, MN (US)

(73) Assignee: Medtronic, Inc., Minneapolis, MN (US)

( * ) Notice: Subject to any disclaimer, the term of this patent is extended or adjusted under 35 U.S.C. 154(b) by 685 days.

(21) Appl. No.: 09/779,537

(22) Filed: Feb. 9, 2001

(65) Prior Publication Data

US 2002/0151796 A1  Oct. 17, 2002

(51) Int. Cl.
*A61B 8/14* (2006.01)

(52) U.S. Cl. .................. 600/462; 600/437; 600/458; 600/459; 424/9.3

(58) Field of Classification Search ........ 600/437–472; 604/6

See application file for complete search history.

(56) References Cited

U.S. PATENT DOCUMENTS

| | | | |
|---|---|---|---|
| 4,207,901 A | 6/1980 | Nigam | |
| 4,582,061 A | 4/1986 | Fry | |
| 4,594,207 A | 6/1986 | Josefiak et al. | |
| 4,805,628 A | 2/1989 | Fry et al. | |
| 4,869,259 A | 9/1989 | Elkins | |
| 5,081,997 A | 1/1992 | Bosley, Jr. et al. | |
| 5,201,314 A | 4/1993 | Bosley et al. | |
| 5,289,831 A * | 3/1994 | Bosley ........................ | 128/899 |
| 5,327,891 A | 7/1994 | Rammler | |
| 5,370,901 A | 12/1994 | Tournier et al. | |
| 5,383,466 A | 1/1995 | Partika | |
| 5,668,188 A | 9/1997 | Whinnery et al. | |
| 5,688,490 A | 11/1997 | Tournier et al. | |
| 5,707,606 A | 1/1998 | Quay | |
| 5,741,478 A | 4/1998 | Osborne et al. | |
| 5,741,522 A * | 4/1998 | Violante et al. ............ | 424/489 |
| 5,759,154 A | 6/1998 | Hoyns | |
| 5,776,496 A * | 7/1998 | Violante et al. ............ | 424/489 |
| 5,792,445 A | 8/1998 | Tournier et al. | |
| 5,921,933 A | 7/1999 | Sarkis et al. | |
| 6,018,676 A | 1/2000 | Davis et al. | |
| 6,104,473 A * | 8/2000 | Konagaya ..................... | 355/55 |
| 6,106,473 A | 8/2000 | Violante et al. | |

FOREIGN PATENT DOCUMENTS

WO    WO 98/19713    5/1998

OTHER PUBLICATIONS

Gomez Alvarez-Arenas, T.E., Gonzalez, A.M., De Frutos, J. and Montero de espinosa, F.R., Piezoelectric Characterisation of Porous Piezoceramics, IEEE Ultrasonics Symposium, 1996, p. 519-522.*

Hillenbrand, J. and Sessler, G.M., Piezoelectric Properties of Polypropylene/Air and Poly(vinylidene fluoride)/Air Composites, 2000 Conference on Electrical Insulation and Dielectric Phenomena, p. 161-165.*

* cited by examiner

*Primary Examiner*—Ali Imam
*Assistant Examiner*—William Jung
(74) *Attorney, Agent, or Firm*—Paul H. McDowall; Girma Wolde-Michael

(57) ABSTRACT

Echogenic devices, and methods of making and using such devices, are disclosed. In one aspect, the devices include a porous polymeric material that is preparable by extracting a phase separated composition. In another aspect, the echogenic devices include a polymeric composition having porous particles therein. Preferably the devices are medical devices.

10 Claims, No Drawings

ECHOGENIC DEVICES AND METHODS OF MAKING AND USING SUCH DEVICES

FIELD OF THE INVENTION

The present invention relates to echogenic devices and methods of making and using such devices.

BACKGROUND

Ultrasonic imaging is widely used in a variety of fields including, for example, the medical field. In the medical field, ultrasonic imaging has found widespread use in applications including, for example, imaging physiological structures and tissue such as organs, tumors, vessels, and the like. In such applications it is often desirable for a physician or technician to have an image of a medical device which has been inserted in the tissue or passageway of a patient. A variety of approaches have been used to enhance the ultrasonic imaging of devices by increasing the acoustic reflection coefficient of the devices. Such approaches include, for example, attempts to alter the surface of the device by altering the geometry of the surface, increasing surface roughness, and fabricating surfaces which may entrap gas.

A few reports of echogenic devices and materials with echogenic and/or porous properties have appeared in the art, some examples of which may be found in the patents and publications listed in Table 1 below.

TABLE 1

Patents and Publications

| Patent/Publication No. | Inventor(s) | Issue/Publication Date |
| --- | --- | --- |
| U.S. Pat. No. 6,106,473 | Violante et al. | Aug. 22, 2000 |
| U.S. Pat. No. 6,018,676 | Davis et al. | Jan. 25, 2000 |
| U.S. Pat. No. 5,921,933 | Sarkis et al. | Jul. 13, 1999 |
| U.S. Pat. No. 5,792,445 | Tournier et al. | Aug. 11, 1998 |
| U.S. Pat. No. 5,759,154 | Hoyns | Jun. 2, 1998 |
| U.S. Pat. No. 5,741,478 | Osborne et al. | Apr. 21, 1998 |
| U.S. Pat. No. 5,707,606 | Quay | Jan. 13, 1998 |
| U.S. Pat. No. 5,688,490 | Tournier et al. | Nov. 18, 1997 |
| U.S. Pat. No. 5,668,188 | Whinnery et al. | Sep. 16, 1997 |
| U.S. Pat. No. 5,383,466 | Partika | Jan. 24, 1995 |
| U.S. Pat. No. 5,370,901 | Tournier et al. | Dec. 6, 1994 |
| U.S. Pat. No. 5,327,891 | Rammler | Jul. 12, 1994 |
| U.S. Pat. No. 5,289,831 | Bosley | Mar. 1, 1994 |
| U.S. Pat. No. 5,201,314 | Bosley et al. | Apr. 13, 1993 |
| U.S. Pat. No. 5,081,997 | Bosley, Jr. et al. | Jan. 21, 1992 |
| U.S. Pat. No. 4,869,259 | Elkins | Sep. 26, 1989 |
| U.S. Pat. No. 4,805,628 | Fry et al. | Feb. 21, 1989 |
| U.S. Pat. No. 4,594,207 | Josefiak et al. | Jun. 10, 1986 |
| U.S. Pat. No. 4,582,061 | Fry | Apr. 15, 1986 |
| U.S. Pat. No. 4,207,901 | Nigam | Jun. 17, 1980 |
| WO 98/19713 | Violante et al. | May 14, 1998 |

All patents and publications listed in Table 1 above are hereby incorporated by reference herein in their respective entireties. As those of ordinary skill in the art will appreciate readily upon reading the Summary of the Invention, Detailed Description of the Preferred Embodiments, and Claims set forth below, many of the devices, materials, and methods disclosed in the patents and publications of Table 1 may be modified advantageously by using the teachings of the present invention.

SUMMARY OF THE INVENTION

The present invention has certain objects. That is, various embodiments of the present invention provide solutions to one or more problems existing in the prior art respecting echogenic devices. Those problems include, for example, devices having surfaces with inadequate echogenicity, inadequate hydrophilicity, inadequate biocompatibility, undue roughness, tackiness, and slipperiness. Methods of making echogenic devices (e.g., coating methods) also suffer from problems including, but not limited to, difficulties in applying coatings to different substrates, excessive coating thicknesses, the complexity of the required coating processes, and incompatibility with related manufacturing processes. Various embodiments of the present invention have the object of solving at least one of the foregoing problems. While some echogenic devices and methods were capable of solving at least some of the foregoing problems, they were generally not employed because of their prohibitively high cost or difficult manufacturing processes. It is therefore another object of the present invention to provide an improved echogenic device that may be manufactured and sold at low cost, yet still fulfill at least one of the foregoing objects.

In comparison to known echogenic devices, various embodiments of the present invention may provide one or more of the following advantages. The present invention provides echogenic devices with improved properties over echogenic devices known in the art. For example, echogenic devices of the present invention preferably have relatively high practical echogenicity. A relatively high practical echogenicity may be important in avoiding complications such as poor sonic imaging properties during surgical procedures.

The present invention also provides advantageous methods for making and using echogenic devices. Methods of the present invention preferably allow the use of simple and uncomplicated methods to produce echogenic devices. Such simple and uncomplicated processes may provide economic advantages as well as product quality improvements. For example, methods of the present invention involving extraction of a phase separated composition to produce a porous polymeric material preferably provide a material with adjustable total pore volume, adjustable pore size, and adjustable pore walls. Adjustable total pore volume, adjustable pore size, and adjustable pore walls may be important factors for tailoring the echogenic properties of the device.

Some embodiments of the present invention preferably include one or more of the following features: medical devices, polymeric materials, porous materials, microporous materials, devices having a polymeric coating layer, devices having a porous coating layer, devices having a microporous coating layer, devices having an echogenic coating layer, devices including porous particles, devices including polymers that are curable by irradiation with ultraviolet light, devices including a coating layer having porous particles, and devices including a coating layer having polymers that are curable by irradiation with ultraviolet light.

DEFINITIONS

As used herein, "echogenic" means giving rise to reflections or echoes of ultrasound waves.

As used herein, "echogenicity" refers to the relative extent that a surface reflects incident ultrasound energy directly back to a sensor, which is proximal to the source or emitter of the ultrasonic energy. The low practical echogenicity of a smooth device hampers accurate imaging of the device within a medium. When the smooth device is oriented at right angles to the ultrasound waves, the ultrasound waves are directly reflected off the device back to the ultrasound transducer, and the device is said to have a relatively high practical echogenicity. At other orientation angles, less of the ultrasound energy is directly reflected back to the transducer, thus reducing the practical echogenicity of the device.

As used herein, "sonically imageable" refers to a material that is detectable by diagnostic echographic equipment, either in a model medium or a human or animal body.

As used herein, "phase separated" refers to a material having a domain-like structure with domains that are observable by optical microscopy, electron microscopy, or by similar methods.

As used herein, "immiscible" means the inability of components to mutually dissolve.

As used herein, "extractable" means the ability of a component to be removed from a mixture by application of an appropriate solvent that does not remove at least one other component of the mixture.

As used herein, "porous" refers to a material that contains pores (either micropores or macropores).

As used herein, "pores" mean hollow cavities, whether at the surface or interior of the material. The hollow cavities may be closed, or they may display openings (e.g. at the surface of the material), and they may display one or more connections to adjacent pores. The hollow cavities that connect individual hollow cavities with one another and frequently deviate in their dimensions from the hollow cavities that they connect, are also designated as pores. The pores can display any suitable regular or irregular geometry, for example, oblong, cylindrical, round, or hollow cavities with irregular form. The radius of a pore as used herein is defined as the radius of a sphere of equal volume to the pore.

As used herein, "micropore" is a hollow space with a radius of at most about 30 nanometers.

As used herein, "macropore" is a hollow space with a radius of greater than about 30 nanometers.

As used herein, "porous particles" refers to porous material (e.g., beads and grains). Porous particles may be any size or shape as desired and are preferably from about 1 micrometer to about 1000 micrometers in size.

As used herein, the term "curing" includes hardening, crosslinking, polymerizing, chain extending, and other related chemical reactions.

As used herein, "curable by irradiation with ultraviolet light" means that a substantial amount of curing is initiated by irradiation with light having a wavelength of about 250 nanometer to about 400 nanometers. Materials that are curable by irradiation with ultraviolet light preferably include compounds that are sensitive to light (e.g., crosslinkers and initiators) that may alter properties of the compound upon curing.

As used herein, a "structural component" refers to an element of a device that provides structure for the device. For example, the body of a device gives the device its characteristic shape and size and provides for strength and integrity of the device. Structural components are to be distinguished from ancillary components such as coatings. Coatings are typically applied to structural components, and thus do not by themselves provide structure for the device.

As used herein, a "biocompatible" surface is one that does not generally cause significant adverse reactions (e.g., toxic or antigenic responses) in the body, whether it degrades within the body, remains for extended periods of time, or is excreted whole. Ideally, a biocompatible surface will not induce undesirable reactions in the body as a result of contact with bodily fluids or tissue, such as tissue death, tumor formation, allergic reaction, foreign body reaction (rejection), inflammatory reaction, or blood clotting, for example.

DETAILED DESCRIPTION OF THE PREFERRED EMBODIMENTS

In one aspect, the present invention provides echogenic devices. In one embodiment, the echogenic device includes a porous polymeric material that is at least a portion of a structural component of the device. Preferably the porous polymeric material is preparable by providing a phase separated composition including a polymer and an extractable material, and extracting the extractable material from the composition. Preferably the device is positionable within a medium. Preferably the device is a medical device for insertion in human or animal tissue.

In another embodiment, the echogenic device is an echogenically enhanced medical device that is preparable by providing a phase separated composition including a polymer and an extractable material; shaping the composition to form at least a portion of a structural component of the device; and extracting the extractable material from the composition.

In another aspect, the present invention provides methods for preparing echogenically enhanced devices. In one embodiment, the method includes providing a phase separated composition including a polymer and an extractable material; shaping the composition to form at least a portion of the device; and extracting the extractable material from the composition. Preferably the method provides a medical device for insertion in human or animal tissue.

In another embodiment, the method includes providing at least a structural component of the medical device; applying a phase separated composition including a polymer and an extractable material to the structural component of the medical device; and extracting the extractable material from the composition.

In another aspect, the present invention provides a method for sonically imaging a device. The method includes providing a device having a porous polymeric material that is at least a portion of a structural component of the device; positioning the device in a sonic imaging beam; and generating an image of the device from the sonic imaging beam. Preferably the porous polymeric material is preparable by providing a phase separated composition comprising a polymer and an extractable material, and extracting the extractable material from the composition.

In another aspect, the present invention provides an echogenic device including a composition that is preparable by curing a polymer having porous particles therein by irradiation with ultraviolet light. Preferably the device is positionable within a medium. Preferably the device is a medical device for insertion in human or animal tissue.

In another aspect, the present invention provides a method for increasing the echogenicity of a device. The method includes providing a polymer that is curable by irradiation with ultraviolet light; blending porous particles with the polymer to produce a composition that is curable by irradiation with ultraviolet light; shaping the composition to form at least a portion of the device; and curing the composition by irradiation with ultraviolet light. Preferably the device is a medical device for insertion in human or animal tissue.

In another aspect, the present invention provides a method for preparing an echogenically enhanced device. The method includes providing at least a structural component of the medical device; providing a polymer that is curable by irradiation with ultraviolet light; blending porous particles with the polymer to produce a composition that is curable by irradiation with ultraviolet light; applying the composition to the structural component of the medical device; and curing the composition by irradiation with ultraviolet light. Preferably the device is a medical device for insertion in human or animal tissue.

The present invention provides echogenic devices, and methods of making and using such devices. In one aspect, the devices include a porous polymeric material as at least a portion of a structural component of the device. Preferably the porous polymeric material is preparable by extracting a phase separated composition. In another aspect, the echogenic devices include a polymeric composition having porous particles therein. In one embodiment, the echogenic portion of the device may be a coating layer on a structural component of the device. In another embodiment, at least a portion of the structural component may be an echogenic composition. The porous portions of the device preferably are capable of entrapping gas when the device is inserted in a medium. Preferably the porous portions of the device are microporous. Preferably the devices are medical devices, and the medium is human or animal tissue.

Echogenic devices of the present invention preferably have useful ultrasonic scattering properties. When sonically imaged, the echogenic device preferably creates high contrast with the medium in which it is inserted. Contrast may be enhanced by entrapped gas or fluid in the porous portions of the surface of the device. The acoustic impedance is defined as the product of the density of a material times the speed of sound in the material. The acoustic impedance of some common materials are listed in Table 2. For imaging a device in a medium, the level of observed contrast may be related to the ratio between the acoustic impedance of the high acoustic impedance material to the low acoustic impedance material.

TABLE 2

Acoustic Impedance of Common Materials

| Material | Acoustic Impedance ($10^6$ kg · m$^{-2}$ · s$^{-1}$) |
|---|---|
| Air | 0.0004 |
| Water | 1.48 |
| Muscle | 1.7 |
| Bone | 7.8 |
| Metal | 75 |

By examining the acoustic impedances listed in Table 2, one can determine that for an aqueous medium such as blood, air has a higher acoustic impedance ratio (1.48/0.0004=3700) and would be expected to provide higher contrast with the medium than would metal (75/1.48=51).

Echogenic devices of the present invention may be useful in a variety of applications including, for example, industrial imaging applications and medical imaging applications. Examples of echogenic devices of the present invention that may have utility as medical devices include, for example, pacemaker leads, stents, central venous catheters and guidewires, midline catheters and guidewires, interventional catheters and guidewires, shunts, cannulas, drainage tubes, vena cava filters, and biopsy needles.

In one aspect, the present invention discloses a porous polymeric material that is preparable by, and preferably prepared by, the extraction of an extractable material from a phase separated composition that includes a polymer and an extractable material. The extractable material is or becomes substantially immiscible in the polymeric material and, thus, becomes substantially phase separated. The phase separation may occur spontaneously or it may be induced by a change in conditions including, for example, temperature, pressure, and time dependent chemical changes.

Suitable phase separated compositions include compositions that are known in the art. The polymeric portion may be organic or inorganic. The extractable material may be organic or inorganic, and solid or liquid. Mixtures or combinations of extractable materials may be used to provide the desired degree of phase separation at the desired conditions. Mixtures or combinations of extractable materials may include solvents and/or non-solvents for the polymeric portion of the phase separated composition. Suitable phase separated compositions are disclosed in U.S. Pat. Nos. 4,594,207 and 5,668,188, herein incorporated by reference.

Suitable polymers for use in the phase separated compositions include homopolymers and copolymers. Examples of suitable polymers include, but are not limited to, polyolefins (e.g., polypropylene and polyethylene), acrylates (e.g., poly (ethyl acrylate) and poly(methyl methacrylate)), vinyl polymers (e.g., poly(vinyl chloride) and poly(vinyl acetate)), polyamides (e.g., polyamide 6 and polyamide 66), polyesters (e.g., poly(ethylene terephthalate) and poly(ethylene naphthenate)), polyurethanes (e.g., BIOMER available from DuPont (Wilmington, Del.) and PELLETHANE available from Dow Chemical Co. (Midland, Mich.)), polycarbonates, silicone rubber, and polytetrafluoroethylene. Other additives may be added to the polymer as desired including, but not limited to, dyes, fillers, molding agents, and antioxidants. When such additives are used, they are preferably added at a level of about 0.01% by weight to about 30% by weight based on the weight of the polymer.

The extractable material may be directly added to the polymeric material, or it may be generated in situ through a chemical reaction. The extractable material is preferably substantially miscible or substantially dispersible in the extraction fluid (e.g., aqueous or non-aqueous liquids, supercritical fluids) and may be extracted by extraction methods known in the art. Extractable materials may be organic or inorganic, and solid or liquid. Extractable materials include, but are not limited to, salts (e.g., sodium chloride, potassium chloride, and sodium iodide), oils (e.g., soy oil, palm grain oil, grapeseed oil, peanut oil, and sunflower oil), and surfactants.

The phase separated material may be treated under the conditions desired to produce the desired level of separation and the desired pore size. Suitable conditions which may be varied to produce the phase separated material include temperature, pressure, and mixing conditions. Extraction of a phase separated material to produce an echogenic device offers advantages over other methods of producing echogenic devices known in the art. For example, selection of the materials and control of the conditions used for the phase separation provide convenient methods to tailor pore size and pore volume to the desired levels.

The extractable material may be extracted by use of a suitable extraction fluid. Suitable extraction fluids preferably substantially dissolve or substantially disperse the material to be extracted. Suitable fluids include aqueous liquids, non-aqueous liquids, and supercritical fluids. The extraction conditions may be varied to effectively extract a substantial portion of the extractable material. For example, temperature, pressure, and extraction time may be varied as desired. Suitable extraction procedures include methods known in the art, for example, immersion in the extraction fluid. After extraction, the dry composition retains the porous structure due to removal of the extractable material.

Preferably, the properties of the porous materials may be adjusted as desired. For example, the total pore volume may be adjusted by adjusting the amount of extractable material that is present in the material to be extracted. Preferably the amount of extractable material in the material to be extracted will be from about 0.01% by weight to about 50% by weight based on the weight of the polymeric material present. Preferably the porous material will have a total pore volume of about 1% by weight to about 50% by weight. Preferably, the porous materials are microporous.

The pore size may be adjusted by any suitable method known in the art. Preferably the pore size is at least about 10 nanometers, more preferably at least about 50 nanometers, and most preferably at least about 1 micrometer. Preferably the pore size is at most about 500 micrometers, more preferably at most about 100 micrometers, and most preferably at most about 10 micrometers.

The total pore volume and the pore size may be adjusted to entrap sufficient echogenic contrast agent (e.g., available under the trade designations LEVOVIST from Schering AG (Germany) and ALBUNEX from Molecular Biosystems (San Diego, Calif.)) to provide contrast when the material is placed in a medium and sonically imaged. For example, the total pore volume may be increased to increase the amount of entrapped contrast agent.

In another aspect, the present invention discloses a composition that is preparable by, and preferably prepared by, curing a polymer having porous particles therein by irradiation with ultraviolet light. Preferably the polymer is curable by irradiation with ultraviolet light. Porous particles may be blended with a polymer that is curable by irradiation with ultraviolet light to prepare the composition. Echogenic devices that are preparable by curing a polymer having porous particles therein by irradiation with ultraviolet light may offer advantages over known echogenic devices incorporating prorous particles. For example, curing the composition with ultraviolet radiation may allow the curing to take place at a preferred temperature. A preferred temperature preferably allows for enhanced dispersion of the particles in the cured material.

Suitable porous particles include commercially available materials including, for example, porous polyethylene beads available under the trade designation STAMYPOR from Dutch State Mines (Galeen, The Netherlands) and hollow glass beads. Preferably the porous particles have sufficient porosity to result in a weight gain of at least about 10% and preferably at least about 30% upon immersion of the dry particles in water. Preferably the particles are from about 1 micrometer to about 1 millimeter in size.

Suitable polymers that are curable by irradiation with ultraviolet light include commercially available materials including, for example, one-part acrylics available under the trade designation UVA4107 and one-part epoxies available under the trade designation VLE4101, both available from Star Technology (Waterloo, Ind.).

Preferably the polymers are curable by irradiation with ultraviolet light having a wavelength of about 250 nanometers to about 400 nanometers. However, some polymers may also be cured by irradiation with visible light having a wavelength of about 400 nanometers to about 700 nanometers. Other forms of irradiation may also be suitable to cure the polymers disclosed in the present invention. Examples of such radiation include, for example, infrared radiation and x-ray radiation. Other additives may be added to the polymer as desired.

The porous particles may be mixed with the polymer by methods known in the art. Suitable mixing methods include, for example, mechanical stirring, shaking, two-roll milling, and ball milling. Preferably, the amount of porous particles that is added to the polymer may be selected to provide the desired level of porosity and/or entrapped gas in the echogenic material. The amount of porous particles added is preferably about 1% by weight to about 50% by weight based on the weight of the polymer.

The polymer containing the porous particles may be cured by irradiation with ultraviolet light. Preferably the polymer containing the porous particles is cured by irradiation with ultraviolet light having a wavelength of about 250 nanometers to about 400 nanometers. However, some polymers may also be cured by irradiation with visible light having a wavelength of about 400 nanometers to about 700 nanometers. Other forms of irradiation may also be suitable to cure some polymers disclosed in the present invention. Examples of such radiation include, for example, infrared radiation and x-ray radiation. Any suitable device known in the art for irradiating the polymer containing the porous particles may be used. Preferably the polymer containing the porous particles is irradiated for about 10 seconds to about 10 minutes at the desired temperature. The temperature during irradiation is preferably about 15° C. to about 90° C.

In one embodiment, the echogenic portion of the device may be a coating layer on a structural component of the device. Preferably the dry thickness of the echogenic coating layer is at least about 1 micrometer and preferably at least about 100 micrometers. Preferably the dry thickness of the echogenic coating layer is at most about 1 millimeter and more preferably at most about 500 micrometers.

The coating layer may be applied from a coating solution. The coating solution is preferably prepared by substantially dissolving or substantially dispersing the polymer and extractable material in a solvent. Solvents useful for coating solutions include solvents that can be removed from the coated device at drying temperatures of about 25° C. to about 200° C. Useful solvents preferably have a boiling point of about 40° C. to about 200° C. Solvents useful in coating solutions of the present invention include, for example, tetrahydrofuran, acetone, ethanol, isopropanol, water, methylene chloride, chloroform, hexane, heptane, xylenes, and toluene.

Coating methods known in the art may be used to apply the coating solution to the device for devices and methods of the present invention. Either batch or continuous coating methods may be used to apply echogenic coatings of the present invention. Suitable coating methods include, but are not limited to, spray-coating, dip-coating, immersion coating, and combinations thereof. When using continuous coating methods, useful coating speeds will depend on factors such as the percent solids of the coating solution, viscosity of the coating solution, and temperature of the coating solution. Preferably, the temperature of the coating solution may be maintained at any temperature desired, for example, at 25° C. Preferably a one-step dip-coating process is used.

After the coating is applied, it may be dried by methods known in the art. Suitable drying methods include, but are not limited to, conduction drying, convection drying, hot air impingement, steam treatment, infrared irradiation, ultraviolet irradiation, and microwave irradiation. Preferably the coating is dried by the application of heat. Preferably the coating layer is dried with air at a temperature of about 10° C. to about 300° C. for about 1 second to about 100 seconds.

Preferably the coating and drying methods are selected to provide a substantially uniform coating. Adequate uniformity may be determined by visually inspecting the coated device to ensure that no uncoated surface of the device is exposed. Preferably the coating and drying methods are selected to provide a coating layer with a substantially uniform thickness. Preferably the coating and drying methods are selected to provide a coating with low surface roughness. Surface roughness may be measured using, for example, laser profilometry.

Preferably the coating may be applied to devices having a variety of surfaces including, for example, metals, plastics, and ceramics. Preferably the coating provides a continuous coating layer with adequate adhesion to the surface of the device.

Preferably the coating layer provides useful properties as desired for the specific device. For example, hydrophilicity and biocompatibility are preferable surface characteristics for medical devices. Other properties that may be provided by coating layers of the present invention include, for example, low tackiness and slipperiness.

In another embodiment, at least a portion of a structural component of the device may be an echogenic composition. At least a portion of the structural component of the device may be prepared by shaping the echogenic composition as desired to form at least a portion of the structural component of the device. Suitable shaping methods are known in the art and include, for example, extrusion, compression molding, and extrusion molding. Structural components that are echogenic compositions may offer advantages over non-echogenic structural components that are coated with echogenic coatings to enchance echogenicity. Advantages may include higher levels of echogenicity and elimination of potential problems from the coating layer (e.g., cracking and delamination).

The echogenic devices of the present invention may be useful when the device is sonically imaged while inserted in a medium. For example, medical devices may be sonically imaged while they are inserted in human or animal tissue to assist in surgical procedures. High contrast between the device and the medium in the sonically produced image may help the surgeon to guide the device to the proper organ in surgical or exploratory procedures. Ultrasound imaging can be carried out by equipment and procedures known in the art including, for example, echoencephalography and echocardiography.

The echogenic devices of the present invention may extend the applicability of ultrasound for placement and tracking of devices including, for example, medical devices. Such medical devices include, but are not limited to, pacemaker leads, stents, central venous catheters and guidewires, midline catheters and guidewires, interventional catheters and guidewires, shunts, cannulas, drainage tubes, vena cava filters, and biopsy needles.

The present invention is illustrated by the following examples. It is to be understood that the particular examples, materials, amounts, and procedures are to be interpreted broadly in accordance with the scope and spirit of the invention as set forth herein.

EXAMPLES

All materials (e.g., tetrahydrofuran and ethanol) are commercially available from vendors (e.g., Aldrich Chemical Co., Milwaukee, Wis.). Deionized water is used for all examples.

Example 1

Polyurethane is dissolved in tetrahydrofuran to prepare a 10% by weight polymer solution. Sodium chloride is milled to the required particle size. The milled sodium chloride crystals are added to the polymer solution to give a coating composition containing 10% by weight sodium chloride.

The coating composition is deposited onto a poly(vinyl chloride) cannula and the coating is dried. The dried coating layer is then extracted with water and dried to form a porous surface layer on the cannula. The porous surface layer will enhance the echogenicity of the cannula.

Example 2

One part of soy oil is added to five parts of polypropylene heated to a temperature higher than its melting point, and the composition is applied to a substrate. After cooling, the surface is then extracted with ethanol. The extracted coating layer is then dried to give a porous surface layer on the substrate. The porous surface layer will enhance the echogenicity of the substrate.

Example 3

Porous polyethylene particles available under the trade designation STAMYPOR from Dutch State Mines (Galeen, The Netherlands) are mixed with an ultraviolet light curable glue. The composition is cured by irradiation with ultraviolet light to form a matrix containing the porous particles. The porous particles will enhance the echogenicity of the matrix.

The complete disclosure of all patents, patent applications, publications, and electronically available material cited herein are incorporated by reference.

The preceding specific embodiments are illustrative of the practice of the invention. It is to be understood, therefore, that other expedients known to those skilled in the art or disclosed herein, may be employed without departing from the invention or the scope of the appended claims. For example, the present invention is not limited to medical devices. The present invention is also not limited to echogenic devices per se, but may find further applications such as, for example, industrial devices requiring surface porosity, for example, filters. The present invention further includes within its scope methods of making and using the echogenic devices described hereinabove.

What is claimed is:

1. An echogenic medical device comprising
   a porous polymeric material having a second acoustic impedance that is at least a portion of a structural component of an echogenic medical device having a first acoustic impedance, and
   a plurality of porous particles,
      wherein said porous particles comprise one of porous polyethylene beads and hollow glass beads,
      wherein the plurality of porous particles are sufficiently porous to result in a weight gain of between about 10% and about 30% upon immersion in an aqueous solution,
      wherein individual particles have a diameter dimension between about one micrometer and about one millimeter, and
      wherein the structural component comprises one of: a medical electrical lead, an implantable stent, a central venous catheter, a guidewire, a midline catheter, an interventional catheter, a shunts, a cannula, drainage tube, a vena cava filter, a biopsy needle.

2. The device of claim 1, wherein the porous polymeric material is preparable by providing a phase separated composition comprising a polymer and an extractable material, and extracting the extractable material from the composition, and wherein the extractable material comprises one of: a salt, an oil material, and a surfactant material.

3. A medical device according to claim 1, wherein the structural component is fabricated from one of: a metal material, a plastic material, a ceramic material, a resin-based material.

4. A method for preparing an echogenically enhanced medical device, the method comprising:
   providing a phase separated composition comprising a polymer and an extractable material;
   shaping the composition to form at least a portion of an echogenic medical device having a first impedance; and
   extracting the extractable material from the composition to create a second acoustic impedance,
   wherein the polymer comprises a plurality of porous particles and the porous particles comprise between about one percent (by weight) and about 50% (by weight) based on the weight of the polymer.

5. A method according to claim 4, wherein the extractable material comprises one of: a salt, an oil material, and a surfactant material.

6. A method according to claim 5, wherein the salt comprises one of: a sodium chloride, a potassium chloride, a sodium iodide.

7. A method according to claim 5, wherein the oil material comprises one of: a soy oil, a palm grain oil, a grapeseed oil, a peanut oil, a sunflower oil.

8. A method for preparing an echogenically enhanced medical device, the method comprising:
   providing at least a structural component of the medical device having a first acoustic impedance;
   providing a polymer that is curable by irradiation with ultraviolet light;
   blending porous particles with the polymer to produce a composition that is curable by irradiation with ultraviolet light;
   applying the composition to the structural component of the medical device; and
   curing the composition by irradiation with one of ultraviolet light radiation and visible light radiation to create a second acoustic impedance, wherein said ultraviolet light radiation has a wavelength of between about 250 nanometers to about 400 nanometers and said visible light radiation has a wavelength of between about 400 nanometers to about 700 nanometers.

9. A method according to claim 8, wherein the medical device comprises at least one of:
   a medical electrical lead, an implantable stent, a central venous catheter, a guidewire, a midline catheter, an interventional catheter, a shunts, a cannula, a drainage tube, a vena cava filter, a biopsy needle.

10. A method according to claim 9, wherein the structural component is fabricated from one of: a metal material, a plastic material, a ceramic material, a resin-based material.

* * * * *